United States Patent
Elhaik et al.

(10) Patent No.: US 6,277,414 B1
(45) Date of Patent: Aug. 21, 2001

(54) AQUEOUS COMPOSITION CONTAINING $H_2O_2$, ACIDS AND AG, PREPARATION METHOD THEREFOR AND USE THEREOF FOR DISINFECTION, HYGIENE AND/OR POLLUTION CONTROL

(75) Inventors: Alain Elhaik, Paris; Raphaël Alex De Nicola, Nice, both of (FR)

(73) Assignee: Sodifra, La Garenne Colombes (FR)

( * ) Notice: Subject to any disclaimer, the term of this patent is extended or adjusted under 35 U.S.C. 154(b) by 0 days.

(21) Appl. No.: 08/849,242

(22) PCT Filed: Dec. 18, 1995

(86) PCT No.: PCT/FR95/01690

§ 371 Date: Sep. 22, 1998

§ 102(e) Date: Sep. 22, 1998

(87) PCT Pub. No.: WO96/18301

PCT Pub. Date: Jun. 20, 1996

(30) Foreign Application Priority Data

Dec. 16, 1994 (FR) .................................................. 94/15193

(51) Int. Cl.⁷ .......................... A01N 59/00; A01N 59/16; A01N 37/16; A61L 2/18

(52) U.S. Cl. .......................... 424/616; 424/601; 424/604; 424/613; 424/614; 424/615; 424/618; 424/619; 514/495; 514/557; 514/970; 422/28; 422/29; 422/37; 426/532; 210/749; 210/759; 210/764

(58) Field of Search ................. 424/613–616, 424/618–619, 601, 604; 514/557–560, 495, 970; 422/28–29, 37; 210/749, 759, 764

(56) References Cited

U.S. PATENT DOCUMENTS

| | | | |
|---|---|---|---|
| 3,035,698 | 5/1962 | Novak | 209/235 |
| 3,702,298 | 11/1972 | Zsoldos, Jr. et al. | 210/754 |
| 4,314,966 | 2/1982 | Kleinmann | 422/28 |
| 4,915,955 | * 4/1990 | Gomori | 424/616 |
| 5,152,996 | 10/1992 | Corey | 424/443 |
| 5,171,454 | 12/1992 | Bockowski | 210/764 |
| 6,103,189 | * 8/2000 | Kralovic | 422/28 |

FOREIGN PATENT DOCUMENTS

| | | |
|---|---|---|
| 41 12 933 A1 | 10/1992 | (DE) . |
| 0 024 219 | 2/1981 | (EP) . |
| 0 087343 | 5/1985 | (EP) . |
| 0 193 416 B1 | 9/1986 | (EP) . |
| 0 370 850 B1 | 5/1990 | (EP) . |
| 2 309 531 | 4/1976 | (FR) . |
| 2 321 301 | 8/1976 | (FR) . |
| 2 321 302 | 8/1976 | (FR) . |
| 2 597 347 | 4/1987 | (FR) . |
| 2 189 394 | 10/1987 | (GB) . |
| 2 257 630 | 1/1993 | (GB) . |
| 91/08981 | 6/1991 | (WO) . |
| 94/04167 | 3/1994 | (WO) . |

OTHER PUBLICATIONS

Chemical Abstracts, vol. 83, No. 15, Oct. 13, 1975, Columbus, Ohio, US; abstract No. 127104, K.Imai et al.: "Effect of heavy metal ions on the growth and iron–oxidizing activity of thiobacillus ferrooxidans" XP002001677 see abstract & Agricol.Biol.Chem., vol. 39, No. 7, 1975, pp. 1349–1354.

Chemical Abstracts, vol. 95, No. 20, Nov. 16, 1981, Columbus, Ohio, US; abstract No. 173205, C.L. Brierley: "Effect of hydrogen peroxide on leach dump bacteria" XP002001678 see abstract & Trans.Am.Inst.Min.,Metal., Pet.Eng.,Soc.Min.Eng.Aime, vol. 266, 1979, pp. 1860–1863.

\* cited by examiner

Primary Examiner—John Pak
(74) Attorney, Agent, or Firm—Ladas & Parry

(57) ABSTRACT

The present invention relates to an aqueous decontaminating composition comprising (A) an amount of $H_2O_2$ less than or equal to 60% by weight, based on the total weight of said composition;

(B) an $RCO_3H/RCO_2H$ mixture, where R is methyl or ethyl, as indicated above, said mixture being present in an amount such that the weight ratio of said mixture to the hydrogen peroxide is between 0.15/1 and 0.85/1;

(C) a silver component as a source of Ag ions, selected from the group consisting of silver salts and complexes, said silver component being present in an amount such that the weight ratio of said silver component to the hydrogen peroxide is between 0.0005/1 and 0.015/1;

(D) a stabilizer present in an amount such that the weight ratio of said stabilizer to the hydrogen peroxide is between 0.0005/1 and 0.025/1; and water to make up to 100% by weight. It further relates to the method of preparation and to the use of said composition.

20 Claims, No Drawings

AQUEOUS COMPOSITION CONTAINING H₂O₂, ACIDS AND AG, PREPARATION METHOD THEREFOR AND USE THEREOF FOR DISINFECTION, HYGIENE AND/OR POLLUTION CONTROL This application is a 371 of PCT/FR95/01690, filed on Dec. 18, 1995.

FIELD OF THE INVENTION

The present invention relates to an aqueous disinfecting and cleaning composition based on $H_2O_2$, acids and Ag, as a novel industrial product.

It further relates to the method of preparation and to the use of this composition on the one hand in the field of disinfection and/or hygiene, especially for disinfecting or sterilizing hospital and industrial premises, surfaces of various materials, storage containers, pipelines, harvests, foodstuffs and drinking water, and on the other hand in the field of pollution control, especially for controlling pollution in the mining industries (in particular in the prevention of acid mine drainage and the destruction of cyanides in the soil).

PRIOR ART

In the field of disinfection, several technical solutions are known which utilize $H_2O_2$: some involve an aqueous composition containing $H_2O_2$, a percarboxylic acid ($RCO_3H$, where R is a $C_1$–$C_2$-alkyl group) and the corresponding carboxylic acid ($RCO_2H$), and others involve an aqueous composition containing $H_2O_2$ and silver in the form of a salt or complex.

Thus EP-A-0 370 850 has disclosed an aqueous composition comprising $H_2O_2$ (6–8% by weight, based on the total weight of said composition), $CH_3CO_3H$ (0.1 to 1% by weight) and $CH_3CO_2H$ (2 to 10% by weight) as a hygiene agent for the disinfection of hemodialysis equipment; this composition can be diluted with water before use.

EP-A-0 193 416 has disclosed an aqueous composition comprising $H_2O_2$ (1 to 8% by weight), $CH_3CO_3H$ (0.005 to 0.1% by weight) and $CH_3CO_2H$ in the amount necessary to attain the equilibrium of the system according to the following equation:

$$H_2O_2+CH_3CO_2H \leftrightarrow CH_3CO_3H+H_2O \tag{1a}$$

said composition being used for rendering contact lenses aseptic.

In its only Example, EP-B-0 087 343 (see top of column 6) has disclosed an aqueous composition comprising $H_2O_2$ (19.9% by weight), $CH_3CO_3H$ (2% by weight), $CH_3CO_2H$ (6.1% by weight), $HNO_3$ (8.0% by weight) as a preservative, hydroxyethanediphosphonic acid (0.3% by weight) as a stabilizer and/or corrosion inhibitor, and $H_2O$ (63.7% by weight), this composition being presented as a disinfecting product which is less corrosive towards metals (especially steel) than Javelle water, on the one hand, and the acid $CH_3CO_3H$, on the other.

FR-A-2 321 302 has disclosed an aqueous composition comprising $H_2O_2$ (25–40% by weight), $RCO_3H$ [and/or $RCO_2H$] (0.5–20% by weight), phosphonic acid (0.25–10% by weight) and $H_2O$ (to make up to 100% by weight) as a microbicidal product, the molar ratio $H_2O_2/RCO_3H$ being greater than or equal to 2/1 and preferably between 3/1 and 50/1. The phosphonic acid component present in the aqueous composition according to FR-A-2 321 302 is a hydroxyalkylpolyphosphonic acid, aminoalkylpolyphosphonic acid or polyaminoalkylenepolyphosphonic acid compound or an Na, K, ammonium or ω-hydroxyalkylammonium salt, this phosphonic acid component acting principally as a corrosion inhibitor.

It is known that a percarboxylic acid is prepared according to equation (1):

$$H_2O_2+RCO_2H \leftrightarrow RCO_3H+H_2O \tag{1}$$

and that, to stabilize concentrated aqueous solutions of $RCO_3H$, it is recommended, especially by FR-A-2 309 531, FR-A-2 321 301 and EP-A-0 024 219, to incorporate $H_2O_2$ into said compositions. In practice, in the case of an acid compound $RCO_3H$ in aqueous solution, an aqueous composition is ultimately obtained which comprises a mixture of $H_2O_2$, $RCO_3H$ and $RCO_2H$ according to equilibrium equation (1) given above.

U.S. Pat. No. 3,035,698, on the other hand, has disclosed an aqueous composition comprising $H_2O_2$ and $Ag^+$ ions as a disinfecting product. However, when the hydrogen peroxide in an aqueous mixture of $H_2O_2+Ag^+$ is concentrated, there is a considerable risk of explosion. To limit this risk, FR-A-2 597 347 envisages a preparative technique which utilizes a strong mineral acid (especially phosphoric acid, nitric acid, hydrobromic acid, hydrochloric acid, sulfuric acid or boric acid) and a stabilizing organic acid (especially tartaric acid, citric acid, maleic acid, malonic acid, 6-acetamidohexanoic acid, hippuric acid or acetoxybenzoic acid).

More precisely, according to FR-A-2 597 347, the method of preparing an aqueous concentrate containing $H_2O_2+Ag^+$ comprises the following steps:

mixing a strong mineral acid (pH<1.6) with a silver salt or a silver complex at a temperature of 50–60° C., the molar ratio strong mineral acid/silver component being greater than or equal to 1;

cooling the resulting mixture to a temperature of 25–30° C. and adding a stabilizing organic acid, optionally together with gelatin; and incorporating $H_2O_2$ into the resulting mixture.

The technical solutions of the prior art, which involve an aqueous composition comprising a mixture of $H_2O_2+RCO_3H+RCO_2H$ or a mixture of $H_2O_2+Ag^+$, are found to have an inadequate disinfecting effect (bactericidal, fungicidal, virucidal, algicidal or parasiticidal effect). The following has been observed in particular:

(α) When aqueous compositions corresponding to said technical solutions of the prior art are sprayed into enclosed spaces containing harmful or undesirable strains, the difference between the decimal logarithm of the concentration of said strains at time T=0 and the decimal logarithm of the concentration of the same strains at time T=2 h is not always greater than or equal to 3 for molds or greater than or equal to 4 for bacteria.

In other words, if $[S]_{T=0}$ is the concentration (number of germs per ml) of a given strain at time T=0 and $[S]_{T=2h}$ is that of the same strain at time T=2 h after exposure to a sprayed aqueous composition for 2 h, the technical solutions of the prior art produce a result (ΔR) given by the relationship $$\Delta R = \log_{10}([S]_{T=0}) - \log_{10}([S]_{T=2h}) \tag{2}$$

which is such that, very often,

ΔR≦3 for molds, and

ΔR≦4 for bacteria.

(β) There are strains, especially strains of *Penicillium verrucosus*, which resist the aqueous compositions of the technical solutions of the prior art comprising a mixture of $H_2O_2+RCO_3H$ (especially $CH_3CO_3H$)+$RCO_2H$ (especially $CH_3CO_2H$) or a mixture of $H_2O_2+Ag^+$.

As far as pollution control is concerned, it should be pointed out that the mining industry has to deal with two major environmental problems: (i) leaching (solubilization) of the metals contained in the soils, due to acid drainage and common to all types of mine, and (ii) contamination of the soils by the cyanides originating particularly from the technique of gold extraction in gold mines and gold works.

Numerous minerals and metals present in mine soils, such as arsenic, selenium and aluminum, can be solubilized and can end up in the subterranean waters and the environment due to acid drainage. The acid drainage of rocks is the result of natural oxidation of the sulfur-bearing ores following their exposure to air and water. These oxidation reactions are often accelerated by certain microorganisms. The chemical and biological reactions cause a lowering of the pH of the water, which then has the property of mobilizing any heavy metal which may be present in the rock residues. If sufficient water is available, it will act as a vehicle and the resulting drainage may contain the products of the acid generation process, typically appreciable amounts of Al, Ca, Si, Mg, Na, K, Fe, other metals and sulfates. This phenomenon causes a negative impact on the quality of the water infiltrating into the environment. By way of example, as sulfur-bearing ores are present throughout the Canadian Shield and in coal mines, the leaching of metals is a very widespread problem in the Canadian mining industries.

Acid generation is the result of a complex process involving a large number of chemical reactions. These reactions can be simply illustrated by the following example of the oxidation of pyrites ($FeS_2$), which is one of the most common sulfur-bearing ores.

The first important reaction is oxidation of the sulfur-bearing ore to ferrous iron, sulfate ions and hydrogen ($H^+$):

$$FeS_2+7/2O_2+H_2O \rightarrow Fe^{2+}+2\ SO_4^{2-}+2\ H^+ \quad (2)$$

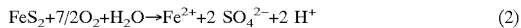

The dissolved iron, the sulfates and the hydrogen cause an increase in the concentration of total dissolved solids and an increase in the acidity of the water. The rise in acidity is associated with a drop in pH. If the neighboring environment is sufficiently oxidizing, most of the ferrous iron will be oxidized to ferric iron ($Fe^{3+}$):

$$Fe^{2+}+\tfrac{1}{4}O_2+H^+ \rightarrow Fe^{3+}+\tfrac{1}{2}\ H_2O \quad (3)$$

At low pH, the ferric iron will precipitate in the form of $Fe(OH)_3$, leaving only a little $Fe^{3+}$ in solution and lowering the pH at the same time:

$$Fe^{3+}+3\ H_2O \rightarrow Fe(OH)_3\ (solid)+3\ H^+ \quad (4)$$

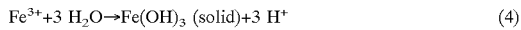

Any $Fe^{3+}$ ion formed in equation 3 and not precipitated in equation 4 can be used to oxidize more pyrites:

$$FeS_2+14\ Fe^{3+}+8\ H_2O \rightarrow 15\ Fe^{2+}+2\ SO_4^{2-}+16\ H^+ \quad (5)$$

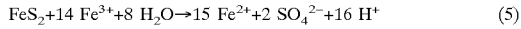

On the basis of these simplified reactions, acid generation, where ferric ions are formed and subsequently precipitated as $Fe(OH)_3$, can be summarized by combining equations 2, 3 and 4:

$$FeS_2+15/4\ O_2+7/2\ H_2O \rightarrow Fe(OH)_3+2\ SO_4^{2-}+4\ H^+ \quad (6)$$

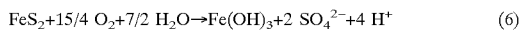

Certain bacteria are found to be capable of accelerating several of reactions 2–5, increasing the acid generation rate by a factor of up to 5. Among these bacteria, strains of *Thiobacillus ferrooxidans* are known to accelerate reactions 2, 3 and 5. It is known that *Thiobacillus ferrooxidans* is particularly involved in the oxidation of pyrites and that it is capable of accelerating the oxidation of the sulfides of As, Cu, Cd, Co, Ni, Sb, Mo, Pb and Zn, thereby increasing the rate or degree of solubilization of these metals. Thus the presence of oxidized arsenic ($AsO_4^{3-}$) in the environment is due to the solubilization of sulfur-bearing ores such as arsenopyrite, realgar, orpiment, cobalite and niccolite. There is therefore a need to prevent acid generation (and hence metal leaching and sulfate formation) by influencing the bacteria, such as *Thiobacillus ferrooxidans*, involved in the oxidation of sulfides.

Furthermore, in the processes for the extraction of metals such as gold, the release of toxic cyanides into the mining residues and the waste waters represents a major environmental problem. The waste waters can be purified by chemical oxidation of the cyanides they contain using an oxidizing agent such as $H_2O_2$ or $SO_2$. On the other hand, nothing is currently being done to treat the soils containing cyanides—the gold mining industry is content for the cyanides to be destroyed by natural atmospheric oxidation mechanisms. There is therefore an urgent need in this area to clean the soils containing cyanides.

OBJECT OF THE INVENTION

According to a first feature of the invention, it is proposed to provide a novel technical solution which makes it possible to overcome the aforementioned disadvantages of the technical solutions of the prior art. This novel technical solution involves an aqueous composition comprising a mixture of $H_2O_2+RCO_3H+RCO_2H+Ag^+$, said mixture making it possible to obtain, especially by spraying into an enclosed space, a $\Delta R$ value greater than 3 for molds and greater than 4 for bacteria after exposure for 2 h.

According to a second feature of the invention, it is proposed to provide, according to said technical solution, an aqueous decontaminating (i.e. disinfecting and/or cleaning) composition comprising a mixture of $H_2O_2$, $RCO_3H$ (where R is ethyl or, preferably, methyl), $RCO_2H$ (where R is defined as indicated above), Ag (in the form of a salt or complex as a source of $Ag^+$ ions) and $H_3PO_4$, in which the four components hydrogen peroxide, percarboxylic acid, carboxylic acid corresponding to said percarboxylic acid and $Ag^+$ have a synergistic effect in respect of the disinfecting and cleaning properties.

According to a third feature of the invention, it is proposed to provide a method of preparing said aqueous decontaminating composition.

According to yet another feature of the invention, it is proposed to use said aqueous decontaminating composition (i) for disinfecting and/or "cold-sterilizing" in particular, or sterilizing at room temperature (10–25° C.), enclosed spaces (hospital, agricultural, industrial, household or transport premises), surfaces of various materials, instruments, storage containers, liquid pipelines, foodstuffs and drinking water, and (ii) for cleaning mining sites in order to prevent acid generation and/or to destroy the cyanides (by oxidation).

SUBJECT OF THE INVENTION

According to the novel technical solution of the invention, an aqueous decontaminating composition is recommended, said composition, which contains $H_2O_2$ and a silver component in an acid medium, comprising (A) an amount of $H_2O_2$less than or equal to 60% by weight, based on the total weight of said composition;

(B) an $RCO_3H/RCO_2H$ mixture, where R is methyl or ethyl, said mixture being present in an amount such that the weight ratio of said mixture to the hydrogen peroxide is between 0.15/1 and 0.85/1;

(C) a silver component as a source of $Ag^+$ ions, selected from the group consisting of silver salts and complexes, said silver component being present in an amount such that the weight ratio of said silver component to the hydrogen peroxide is between 0.0005/1 and 0.015/1;

(D) a stabilizer present in an amount such that the weight ratio of said stabilizer to the hydrogen peroxide is between 0.0005/1 and 0.025/1; and water to make up to 100% by weight.

The method of preparing said aqueous decontaminating composition according to the invention comprises steps consisting in (1°) preparing an aqueous solution of the silver component which is present as a source of $Ag^+$ ions;

(2°) introducing the stabilizer into said resulting solution obtained in this way;

(30°) introducing said resulting solution obtained in this way into the hydrogen peroxide solution or introducing the hydrogen peroxide solution into said resulting solution;

(4°) introducing, into said resulting solution obtained in this way, an acid substance selected from the group consisting of $RCO_3H$, $RCO_2H$ and mixtures thereof, i.e. $RCO_3H+RCO_2H$;

(5°) leaving said resulting solution obtained in this way until the equilibrium $H_2O+RCO_2H \leftarrow\rightarrow RCO_3H+H_2O$ has been established; and (60°) making up to 100% by weight with water.

The use of the aqueous decontaminating composition according to the invention as a disinfecting product comprises (i) a surface or volume treatment of the product to be disinfected or decontaminated, at a temperature of between 0° C. and 50° C., preferably at room temperature (RT) within the range 10° C. to 25° C., with said aqueous disinfecting composition, optionally diluted, and then (ii) the drying of said product treated in this way.

The use of said aqueous composition as a cleaning product comprises step (i) above, the drying of step (ii) taking place of its own accord at room temperature.

The product to be disinfected comprises especially enclosed spaces (particularly hospital, agricultural and industrial premises), surfaces of various materials, instruments, storage containers, pipelines (especially pipelines for aqueous liquids such as water, milk, beer and fruit juice), foodstuffs, harvests, outdoor or greenhouse crops and drinking water.

The product to be cleaned consists especially of soils and waste heaps in the mining industry.

DETAILED DESCRIPTION OF THE INVENTION

Hereafter, unless indicated otherwise, the respective amounts of the ingredients of the aqueous decontaminating composition according to the invention are expressed in % by weight and the dilutions of said composition are expressed as the ratio initial volume/volume of the resulting diluted composition.

In general terms, the aqueous decontaminating composition according to the invention has an $H_2O_2$ content which is less than or equal to 60% by weight, based on the weight of said composition. For said aqueous composition, the lowest antibacterial dose tested corresponds to a final dilution of $5/10^7$ (containing 0.000025% by weight of $H_2O_2$); at this dose, the composition according to the invention provides antibacterial protection for at least 48 h (in the field of balneotherapy).

Consequently, in the vast majority of cases, the present invention recommends a composition which comprises 0.1 to 60% by weight of $H_2O_2$ and which can be diluted at the appropriate time during use.

Hydrogen peroxide presents difficulties as regards transportation when using hydrogen peroxide solution with a high $H_2O_2$ content, for example an $H_2O_2$ content greater than 16% or 8% by weight, depending on the regulations in several countries. If, from a practical point of view, it is advantageous to use hydrogen peroxide solution containing 50 to 70% by weight of $H_2O_2$ as a starting material, the aqueous disinfecting composition according to the invention should preferably have an $H_2O_2$ content which is less than or equal to 8% by weight, so as to avoid special vented packaging to comply with the national regulations for restricting transport, said packaging requiring qualified personnel to use it.

In practice, the aqueous decontaminating composition according to the invention will have an $H_2O_2$ content of the order of 7.5–8% by weight and will be diluted with water, at the time of use, down to a final $H_2O_2$ concentration particularly of between 0.0000025 and 4% by weight.

As a variant, it is possible to market an optionally prediluted, aqueous disinfecting or cleaning composition which is stabilized and contains 1.5 to 8% by weight of $H_2O_2$, is ready to use and retains its efficacy for at least two years.

In practice, the aqueous decontaminating composition according to the invention will advantageously contain 7.5 to 8% by weight of $H_2O_2$ and, if appropriate, will be diluted with $H_2O$ by the user.

The respective amounts of $RCO_3H$ and $RCO_2H$ in the $RCO_3H/RCO_2H$ mixture are not critical. Given equilibrium reaction (1) above, it suffices to have either $H_{22}O$ and $RCO_3H$ or $H_2O_2$ and $RCO_2H$ together in $H_2O$ in order to produce a ternary mixture of $H_2O_2+RCO_3H+RCO_2H$, provided that $H_2O_2$ is in excess relative to the $RCO_3H/RCO_2H$ pair. It therefore suffices, as it were, to incorporate (i) $RCO_2H$ in the presence of $H_2O_2$, or (ii) $RCO_3H$ (which, in the concentrated state, generally contains $H_{22}O$ and $RCO_2H$ according to documents FR-A-2 321 301 and FR-A-2 321 302 cited above) into $H_2O$ in order to produce the combination of $H_2O_2+RCO_3H+RCO_2H$ in equilibrium.

In the aqueous decontaminating composition according to the invention, the weight ratio of the $RCO_3H/RCO_2H$ mixture to the hydrogen peroxide is between 0.15/1 and 0.85/1. In practice, this weight ratio will advantageously be between 0.5/1 and 0.7/1.

In general terms, the $CH_3CO_3H/CH_3CO_2H$ pair (i.e. R=methyl) is preferred to the $CH_3CH_2CO_3H/CH_3CH_2CO_2H$ pair (i.e. R=ethyl) since the first pair is more active than the second as a disinfecting/cleaning means in the aqueous composition according to the invention.

In increasing order of preference, the recommended silver component will be a silver complex, a silver salt with an organic acid (especially $CH_3CO_2Ag$) or a silver salt with a mineral acid (especially $Ag_2SO_4$ and preferably $AgNO_3$).

Silver oxides, $Ag_2O$ and $AgO$, are unsuitable because they are not water-soluble. If $Ag_2O$ and/or $AgO$ were used, it would be necessary firstly to solubilize them with a relatively large amount of a strong base (NaOH or KOH) and then to increase the initial amounts of the $RCO_3H/RCO_2H$ mixture (component B above), on the one hand, and those of the acid stabilizer (component D above), on the other, so as (α) to neutralize the strong base and (β) to have the required amounts of components B and D in the aqueous decontaminating composition.

In the aqueous decontaminating composition according to the invention, the weight ratio of the silver component to the hydrogen peroxide is between 0.0005/1 and 0.015/1. In practice, this weight ratio will advantageously be between 0.0008/1 and 0.005/1 and preferably of the order of 0.001/1.

The stabilizer, which is present (i) to protect the $H_2O_2$ and the $Ag^+$ ions during the preparation of the aqueous decontaminating composition according to the invention and avoid any risk of explosion, especially from concentrated solutions of $H_2O_2$ and $Ag^+$, and (ii) to preserve the required concentrations between $H_2O_2$, $CH_3CO_3H$ and $Ag^+$ in said composition until it is used, is selected from the group consisting of mineral and organic acids. The most effective of these acids are strong mineral acids, the most valuable here being $H_3PO_4$, which is very particularly preferred.

In the aqueous decontaminating composition according to the invention, the weight ratio of the stabilizer to the hydrogen peroxide is between 0.0005/1 and 0.025/1. In practice, this weight ratio will advantageously be between 0.0008/1 and 0.005/1 and preferably of the order of 0.001/1.

According to the invention, it is recommended advantageously to use the stabilizer in an amount which is substantially identical to or slightly greater than that of the silver component.

The aqueous disinfecting composition according to the invention can also contain at least one component selected from the group consisting of (E) a surfactant;

(F) a corrosion inhibitor; and (G) a fragrance.

The surfactant used here is (i) an ionic or non-ionic surface-active compound suitable in particular for contact with foodstuffs and, if appropriate, suitable for oral administration with drinking water at the use dose in question, or (ii) a mixture of such compounds.

Among the products suitable for this purpose, particular mention may be made of alkylbenzenesulfonates, alkylsulfates and alkanesulfonates of alkaline earth metals and (preferably) alkali metals (particularly Na or K), as well as polyethoxylated phosphoric acid alkyl esters and mixtures thereof.

In the aqueous decontaminating composition according to the invention, the weight ratio of the surfactant to the hydrogen peroxide is between 0.00005/1 and 0.01/1. In practice, this weight ratio will advantageously be of the order of 0.005/1.

It is recommended to incorporate a corrosion inhibitor into the aqueous decontaminating composition according to the invention, said corrosion inhibitor, at the dose use, being suitable for contact with foodstuffs and/or for oral administration with drinking water. As corrosion inhibitors which can be used for this purpose, particular mention may be made of the aminophosphonic acids described in FR-A-2 321 302 cited above, their sodium, potassium, ammonium and alkanolamine salts and mixtures thereof. Hydroxyethanediphosphonic, dimethylaminomethanediphosphonic and ethylenediaminotetrakis (methylenephosphonic) acids, their Na, K, $NH_4^+$ or alkanolamine salts and mixtures thereof are particularly suitable for the aqueous decontaminating composition according to the invention. 1,2,3-Benzotriazole is also suitable as a corrosion inhibitor.

In practice, the corrosion inhibitor will be present at a low concentration in the aqueous decontaminating composition according to the invention. When present, said corrosion inhibitor will be used especially in an amount such that the weight ratio of said corrosion inhibitor to the hydrogen peroxide is between 0.00005/1 and 0.03/1 and preferably between 0.001/1 and 0.005/1. As the aqueous decontaminating composition according to the invention contains corrosive acid substances, namely $RCO_3H$, $RCO_2H$ and the stabilizing acid component of item D ($H_3PO_4$), it is important to limit the corrosion so that the corrosion rate of steel or copper articles subjected to 200 immersion cycles in the aqueous decontaminating composition according to the invention, followed by drying (without rinsing), or to 200 spraying cycles with said composition, followed by drying at 15–35° C. (oven or stream of purified air; without rinsing with water), is less than 50 μm/year.

In fact, as the corrosion of metal surfaces is principally the result of a phenomenon called "pitting", it is essential to avoid the formation of said pits, where the germs which it is desired to eradicate would reside and develop.

The fragrant component of item (G) will be used in the aqueous decontaminating composition in an amount which is less than or equal to that of the corrosion inhibitor of item (F).

The water which forms part of the decontaminating composition according to the invention is advantageously a purified water, namely distilled water, demineralized water or, preferably, deionized water. Here the deionized water will preferably be a water having a resistivity greater than $10^5$ Ω/cm and preferably greater than $10^6$ Ω/cm.

The water optionally used to dilute said decontaminating composition according to the invention will advantageously be purified water as indicated above.

The pH of the aqueous composition according to the invention (before use) is generally between 1.5 and 4. It is regulated by means of the preferred component D, $H_3PO_4$.

The aqueous decontaminating composition which is particularly recommended comprises (A) 1.5 to 8% by weight of $H_2O_2$;

(B) 0.75 to 5.6% by weight of a mixture of $RCO_3H$ and $RCO_2H$, where R is ethyl or, preferably, methyl;

(C) 0.0012 to 0.04% by weight of a silver component selected from silver complexes and salts as a source of $Ag^+$ ions;

(D) 0.0012 to 0.04% by weight of $H_3PO_4$;

(E) if appropriate, 0.0075 to 0.04% by weight of surfactant;

(F) if appropriate, 0.003 to 0.04% by weight of corrosion inhibitor;

(G) if appropriate, a fragrance; and water (distilled, demineralized or deionized) to make up to 100% by weight.

A stock solution with an $H_2O_2$ content of the order of 7.5–8% by weight is recommended more particularly. This stock solution contains (A) 7.5–8% by weight of $H_2O_2$;

(B) 4.5 to 4.8% by weight of a mixture of $CH_3CO_3H$+ $CH_3CO_2H$;

(C) 0.008% by weight of $AgNO_3$;

(D) 0.008% by weight of $H_3PO_4$; and water (distilled, demineralized or deionized) to make up to 100% by weight.

Said stock solution is then used either as such or diluted with purified water to an $H_2O_2$ content of 1.5 to 4% by weight;

or complemented with components (E), (F) and/or (G) and then, if necessary, diluted with purified water to an $H_2O_2$ content of 1.5 to 4% by weight;

or complemented with mixture (B) of $CH_2CO_3H+CH_3CO_2H$ until the content of said mixture in the aqueous decontaminating composition is 5.6% by weight, the resulting composition then being diluted with purified water as indicated above, if necessary;

or complemented on the one hand with mixture (B) and on the other hand with components (E), (F) and/or (G), and then, if appropriate, diluted with water as indicated above.

When the preparative method referred to above in the section "Subject of the invention" is carried out, steps (1°) and particularly (2°) to (4°) and (6°) are performed with stirring. In practice, steps (3°) and (4°) are carried out at a temperature less than or equal to 30° C. and preferably at a temperature less than or equal to 25° C., and step (2°) is carried out at a temperature less than or equal to 60° C.

In step (1°), the source of $Ag^+$ ions will preferably be $AgNO_3$. In step (2°), a concentrated aqueous solution of phosphoric acid, in particular a commercial solution containing 85% by weight of $H_3PO_4$, may be used as the stabilizer.

In step (3°), hydrogen peroxide solution with an $H_2O_2$ content greater than 8% by weight and less than or equal to 70% by weight is used; either the solution obtained in step (2°) is introduced into said hydrogen peroxide solution, or said hydrogen peroxide solution is introduced into the solution obtained in step (2°); each of these introductions is carried out slowly (especially at a rate of 1 to 5 liters of solution introduced in 20–60 minutes), with stirring and with cooling to a temperature less than or equal to 30° C. and preferably to a temperature less than or equal to 25° C.

In step (4°), the acid substance ($RCO_3H$, $RCO_2H$ or the mixture of $RCO_3H+RCO_2H$) is introduced into the solution obtained in step (3°), under the same conditions as in said step (3°) as regards the introduction rate, temperature and stirring.

In step (5°), the solution obtained in step (4°) is left to stand for about 48 h at a temperature less than or equal to 30° C. and preferably at a temperature less than or equal to 25° C., so that the equilibrium of equation (1) is established. Step (5°) is advantageously carried out in the dark.

As indicated above, the water used to prepare the aqueous decontaminating composition according to the invention, especially in steps (1°) and (6°), is purified water, i.e. distilled, demineralized or deionized water.

Components (E), (F) and/or (G) are introduced in appropriate manner between step (1°) and step (6°). As a variant, each of these ingredients can be incorporated at the end of step (6°).

The aforementioned stock solution containing 7.5–8% by weight of $H_2O_2$ is prepared by a particular method which comprises steps consisting in (1°) preparing a solution of $AgNO_3$ in part of the total amount of water required to produce said aqueous disinfecting composition;

(2°) introducing, into the resulting solution obtained in this way, an aqueous solution of phosphoric acid containing 85% by weight of $H_3PO_4$;

(3°) introducing the resulting solution obtained in this way into an aqueous solution of hydrogen peroxide containing 50 to 60% by weight of $H_2O_2$, with stirring, at a temperature of between 0° C. and 25° C. and preferably at a temperature of between 4° C. and 15° C., and with introduction of the solution obtained in step (2°) at a rate of between 3 and 6 l/h;

(4°) introducing the acid substance $CH_3CO_2H$ into the resulting solution obtained in this way, with stirring, at a temperature of between 0° C. and 25° C. and preferably at a temperature of between 4° C. and 15° C., and with introduction of the acid substance $CH_3CO_2H$ at a rate of between 3 and 6 l/h;

(5°) leaving the resulting solution obtained in this way to stand for 48 h, in the dark, at a temperature of between 0° C. and 25° C. and preferably at a temperature of between 4° C. and 15° C., so that the equilibrium

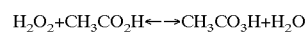

is established; and (6°) adding the remaining water to make up to 100% by weight.

In step (4°) of the preparation of the stock composition, the acid can be introduced in the form of an aqueous solution.

When the aqueous decontaminating composition according to the invention is employed as a disinfecting composition, as is generally the case, it is used (i) as prepared, or (ii) at a rate of at least 5 ml of said composition for a volume of 1 m³ or surface of 1 m² to be treated, said composition being diluted if appropriate.

As regards the use of the aqueous composition according to the invention as a disinfectant, the following is more particularly recommended:

(α) immersion of the product to be treated (which has advantageously been washed beforehand) in an aqueous decontaminating composition containing 1.5 to 4% by weight of $HO_2O_2$;

(β) spraying of an aqueous disinfecting composition containing 2 to 4% by weight of $H_2O_2$ onto a surface to be treated (this is the case of outdoor crops) at a rate of 5 to 20 liters of said composition per hectare;

(γ) spraying of an aqueous disinfecting composition containing 2 to 8% by weight of $H_2O_2$ into a volume to be treated (this is the case of food harvests in silos) at a rate of 0.5 to 4 liters of said composition per m³; or (δ) incorporation of an aqueous disinfecting composition containing 16 to 50% by weight of $H_2O_2$ into the water to be treated (this is the case particularly of swimming pool water or drinking water) at a rate of 5 to 150 ml of said composition per 1 m³ of water to be treated (5 to 150 ml corresponding to a final use concentration of 0.00008% by weight to 0.0075% by weight of $H_2O_2$); in particular, for the disinfection of drinking water, about 20 ml/m³ will be used (i.e. a final use concentration of the order of 0.001% by weight of $H_2O_2$).

The aqueous disinfecting composition according to the invention is especially useful for:

(a) the disinfection and hygiene of hospital premises and industrial premises (milk dairies, cheese dairies, malt houses, breweries, greenhouses, cowsheds, hen houses, stables, packaging lines for foodstuffs, drinks or drugs, interiors of aeroplanes and boats) and the contents of said premises, especially the equipment or instruments equipping said premises or used therein;

(b) the disinfection and hygiene of storage containers (especially silos) and pipelines for conveying liquid or solid products such as foodstuffs (sugar, tea, coffee, cereals, drinks);

(c) the disinfection and hygiene of swimming pools and the contents of the aforementioned storage containers and pipelines;

(d) the disinfection of drinking water; or (e) the protection of outdoor crops (cereals, tomatoes, forests, banana plantations, orchards, etc.), by virtue of its bactericidal, fungicidal, sporicidal, virucidal and antiparasitic properties.

When employed as a cleaning composition, the composition according to the invention is used either by being sprayed into the volume to be treated or onto a surface of said volume, or else by being stirred in.

In practice, the starting composition, like the aforementioned stock composition, will contain 7.5 to 8% by weight of $H_2O_2$ and will be diluted before use to a final use dilution of less than 1/100 (preferably a dilution of 5/1000 to 5/10,000 and particularly preferably of 1/1000).

The cleaning composition according to the invention is mainly effective in mining sites, especially for eliminating or substantially reducing (i) acid generation (particularly from sulfur-bearing ores) and (ii) cyanides (particularly in the case of gold mines and gold extraction plants).

Best Mode

The best mode of carrying out the invention consists in using a stock composition which, as indicated above, contains (A) 7.5–8% by weight of $H_2O_2$;

(B) 4.5 to 4.8% by weight of a mixture of $CH_3CO_3H$ + $CH_3CO_2H$;

(C) 0.008% by weight of $AgNO_3$;

(D) 0.008% by weight of $H_3PO_4$; and distilled, demineralized or deionized water to make up to 100% by weight.

This stock composition is then complemented with components (E), (F) and/or (G) mentioned above and, if appropriate, components (B), (C) or (D).

Other advantages and characteristics of the invention will be understood more clearly from the following description of practical Examples and comparative experiments. Of course, these data taken as a whole do not in any way imply a limitation but are given by way of illustration.

In these experiments, the "IP" strains used are those which were supplied by the Collection Nationale de Cultures de Microorganismes (CNCM) administered by the Institut Pasteur in Paris.

EXAMPLES 1–5

The formulations of the Examples (Ex. 1–Ex. 5) according to the invention, and the formulations of the Comparative Examples according to the prior art without silver component (A1–A5) or without the $RCO_3H/RCO_3H$ mixture (B1–B5), have been collated in Table Ia ($CH_3CO_2H$/$CH_3CO_3H$ pair) and Table Ib ($EtCO_2H$/$EtCO_3H$ pair) below, composition B4 of Table Ib being identical to that of composition B1 of Table Ia, and the water present in these formulations (not mentioned in said Tables Ia and Ib) representing the amount required to make up to 100% by weight.

TABLE Ia

Formulations (% by weight) of the ingredients other than the water

| Product | $H_2O_2$ | Mixture of $CH_3CO_2H$ + $CH_3CO_3H$ | $AgNO_3$ | $H_3PO_4$ | Surfactant (a) | Corrosion inhibitor (b) |
|---|---|---|---|---|---|---|
| Ex. 1 | 8 | 4.8 | 0.008 | 0.008 | 0.04 | 0.032 |
| A1 | 8 | 4.8 | — | 0.008 | 0.04 | 0.032 |
| B1 | 8 | — | 0.008 | 0.008 | 0.04 | 0.032 |
| Ex. 2 | 8 | 5.6 | 0.005 | 0.005 | 0.04 | 0.032 |
| A2 | 8 | 5.6 | — | 0.005 | 0.04 | 0.032 |
| B2 | 8 | — | 0.005 | 0.005 | 0.04 | 0.032 |
| Ex. 3 | 7.75 | 4.5 | 0.002 | 0.004 | 0.02 | 0.02 |
| A3 | 7.75 | 4.5 | — | 0.004 | 0.02 | 0.02 |
| B3 | 7.75 | — | 0.002 | 0.004 | 0.02 | 0.02 |

Notes: see Table Ib

TABLE Ib

Formulations (% by weight) of the ingredients other than the water

| Product | $H_2O_2$ | Mixture of $Et_3CO_2H$ + $Et_3CO_3H$ | $AgNO_3$ | $H_3PO_4$ | Surfactant (a) | Corrosion inhibitor (b) |
|---|---|---|---|---|---|---|
| Ex. 4 | 8 | 4.8 | 0.008 | 0.008 | 0.04 | 0.032 |
| A4 | 8 | 4.8 | — | 0.008 | 0.04 | 0.032 |
| B4 (c) | 8 | — | 0.008 | 0.008 | 0.04 | 0.032 |
| Ex. 5 | 8 | 5.6 | 0.01 | 0.01 | 0.04 | 0.032 |
| A5 | 8 | 5.6 | — | 0.01 | 0.04 | 0.032 |
| B5 | 8 | — | 0.01 | 0.01 | 0.04 | 0.032 |

Notes:
(a): 1/1 (w/w) mixture of sodium alkylbenzenesulfonate and ammonium alkyl sulfate
(b): 1/3 (w/w) mixture of hydroxyethanediphosphonic acid and dimethylaminomethanediphosphonic acid
(c): B4 is identical to B1

EXAMPLE 6

A concentration composition according to the invention was prepared which comprised:

| | |
|---|---|
| $H_2O_2$ | 50% by weight |
| mixture of $CH_3CO_2H$ + $CH_3CO_3H$ | 30% by weight |
| $AgNO_3$ | 0.05% by weight |
| $H_3PO_4$ | 0.05% by weight |
| surfactant | 0.25% by weight |
| corrosion inhibitor | 0.20% by weight |
| $H_2O$ to make up to | 100% by weight |

This composition is diluted to the required $H_2O_2$ concentration at the time of use.

EXAMPLE 7

A stock cleaning composition according to the invention was prepared which comprised:

| | |
|---|---|
| $H_2O_2$ | 7.8% by weight |
| mixture of $CH_3CO_2H$ + $CH_3CO_3H$ | 4.7% by weight |
| $AgNO_3$ | 0.008% by weight |
| $H_3PO_4$ | 0.008% by weight |
| surfactant | 0.04% by weight |
| $H_2O$ to make up to | 100% by weight |

This stock composition is diluted to a final use dilution of less than 1/100 at the time of use.

Analogous compositions A7 and B7 were likewise prepared for comparison, said compositions differing from Ex. 7 only in the absence of $AgNO_3$ (composition A7) or in the absence of the mixture of $CH_3CO_2H+CH_3CO_3H$ (composition B7).

Experiments I

The bactericidal, fungicidal and sporicidal activities of the compositions according to the invention were measured, against the comparative compositions, by spraying according to French Standard AFNOR NF 72 281 (as revised in December 1989) under the following operating conditions:

| | |
|---|---|
| Spraying apparatus | AEROBRUMEUR ® type H |
| Output | 16 ml/m³ |
| Amount of test product | 540 ml |
| Diffusion time of the test product (i.e. composition) | 12 minutes |
| Experimental enclosure volume | 33 m³ |
| temperature | 23–24° C. |
| relative humidity | 85% (initial), 80% (final) |
| Support | microscope slides for bacteriology or mycology |
| Distance of the support from the source | 1.2 m |
| Exposure time of the support | 2 h |
| Recovery liquid | sterile distilled water + TWEEN ® 80 (0.5% by weight) |
| Volume of the recovery liquid | 100 ml |
| Membrane rinsing volume | 100 ml |
| Number of rinses | 3 |

The results obtained have been collated in Tables IIa to IIe below, which show the concentrations of the test products (i.e. compositions Ex. 1–Ex. 5, A1–A5 and B1–B5) after dilution with deionized water.

TABLE IIA

| | Ex. 1 dilution: 1/5 | | | A1 dilution: 1/5 | | B1 dilution: 1/5 | |
|---|---|---|---|---|---|---|---|
| Strain | (1) | (2) | (3) | (2) | (3) | (2) | (3) |
| Staphylococcus aureus IP 52 154 | $1.8 \times 10^6$ | 0 | 6.25 | 0 | 6.25 | 0 | 6.25 |
| Pseudomonas aeruginosa IP A22 | $1.5 \times 10^6$ | 0 | 6.17 | $1.9 \times 10$ | 4.90 | $2.1 \times 10$ | 4.85 |
| Enterococcus faecium IP 5 855 | $1.6 \times 10^5$ | 0 | 5.20 | 10 | 4.20 | $9 \times 10$ | 3.25 |
| Mycobacterium smegmatis IP 7 326 | $1.3 \times 10^5$ | 0 | 5.11 | $2 \times 10$ | 3.81 | $1.9 \times 10$ | 3.84 |
| Candida albicans IP 1180 79 | $1.9 \times 10^5$ | 0 | 5.27 | $1.8 \times 10$ | 4.02 | $1.5 \times 10$ | 4.10 |
| Penicillium verrucosum IP 1186 79 | $1.5 \times 10^5$ | 0 | 5.17 | $2.3 \times 10^2$ | 2.81 | $2.7 \times 10^2$ | 2.74 |
| spores of Bacillus subtilis var. Niger IP 7 718 (a) | $3.9 \times 10^3$ | 0 | 3.59 | $8.1 \times 10$ | 1.69 | $8.4 \times 10$ | 1.67 |

Notes:
(1) number of germs (or spores)/ml at time T = 0, i.e. $[S]_{\tau=0}$
(2) number of germs (or spores)/ml at time T = 2 h, i.e. $[S]_{\tau=2h}$
(3) germicidal (or sporicidal) activity, i.e. $\Delta R = \log([S]_{\tau=0}) - \log([S]_{\tau=2h})$ TABLE IIb

| | Ex. 2 dilution: ½ | | | A2 dilution: ½ | | B2 dilution: ½ | |
|---|---|---|---|---|---|---|---|
| Strain | (1) | (2) | (3) | (2) | (3) | (2) | (3) |
| Staphylococcus aureus IP 52 154 | $1.8 \times 10^6$ | 0 | 6.25 | 0 | 6.25 | 0 | 6.25 |
| Pseudomonas aeruginosa IP A22 | $1.5 \times 10^6$ | 0 | 6.17 | 0 | 6.17 | 0 | 6.17 |

TABLE IIb-continued

| | | Ex. 2 dilution: ½ | | A2 dilution: ½ | | B2 dilution: ½ | |
|---|---|---|---|---|---|---|---|
| Strain | (1) | (2) | (3) | (2) | (3) | (2) | (3) |
| Enterococcus faecium IP 5 855 | $1.6 \times 10^5$ | 0 | 5.20 | 0 | 5.20 | 5 | 4.61 |
| Mycobacterium smegmatis IP 7 326 | $1.4 \times 10^5$ | 0 | 5.14 | 0 | 5.14 | 10 | 4.14 |
| Candida albicans IP 1180 79 | $1.9 \times 10^5$ | 0 | 5.27 | 5 | 4.58 | 10 | 4.27 |
| Penicillium verrucosum IP 1186 79 | $1.5 \times 10^5$ | 0 | 5.17 | $2 \times 10^2$ | 2.87 | $2.3 \times 10^2$ | 2.81 |
| spores of Bacillus subtilis var. Niger IP 7 718 (a) | $3.9 \times 10^3$ | 0 | 3.59 | $4.8 \times 10$ | 1.91 | $5.1 \times 10$ | 1.89 |

Notes:
(1) number of germs (or spores)/ml at time T = 0, i.e. $[S]_{\tau=0}$
(2) number of germs (or spores)/ml at time T = 2 h, i.e. $[S]_{\tau=2h}$
(3) germicidal (or sporicidal) activity, i.e. $\Delta R = \log([S]_{\tau=0}) - \log([S]_{\tau=2h})$

TABLE IIc

| | | Ex. 3 dilution: 1/10 | | A3 dilution: 1/10 | | B3 dilution: 1/10 | |
|---|---|---|---|---|---|---|---|
| Strain | (1) | (2) | (3) | (2) | (3) | (2) | (3) |
| Staphylococcus aureus IP 52 154 | $2.1 \times 10^6$ | 10 | 5.32 | $1.1 \times 10^2$ | 4.28 | $1.2 \times 10^2$ | 4.25 |
| Pseudomonas aeruginosa IP A22 | $1.4 \times 10^6$ | 10 | 5.14 | $3.5 \times 10$ | 3.60 | $3.7 \times 10$ | 3.58 |
| Enterococcus faecium IP 5 855 | $1.3 \times 10^5$ | 0 | 5.11 | $10^2$ | 3.11 | $1.7 \times 10^2$ | 2.88 |
| Hycobacterium smegmatis IP 7 326 | $1.5 \times 10^5$ | 0 | 5.17 | $1.9 \times 10^2$ | 2.89 | $2.2 \times 10^2$ | 2.87 |
| Candida albicans IP 1180 79 | $1.7 \times 10^5$ | 10 | 4.23 | $2.8 \times 10^2$ | 2.78 | $3.1 \times 10^2$ | 2.73 |
| Penicillium verrucosum IP 1186 79 | $1.1 \times 10^5$ | $1.3 \times 10$ | 3.82 | $6.7 \times 10^2$ | 2.21 | $1.1 \times 10^5$ | 2.00 |
| spores of Bacillus subtilis var. Niger IP 7 718 (a) | $4.2 \times 10^5$ | 0 | 3.62 | $1.3 \times 10^2$ | 1.51 | $1.9 \times 10^2$ | 1.34 |

Notes:
(1) number of germs (or spores)/ml at time T = 0, i.e. $[S]_{\tau=0}$
(2) number of germs (or spores)/ml at time T = 2 h, i.e. $[S]_{\tau=2h}$
(3) germicidal (or sporicidal) activity, i.e. $\Delta R = \log([S]_{\tau=0}) - \log([S]_{\tau=2h})$

TABLE IId

| | | Ex. 4 dilution: 1/5 | | A4 dilution: 1/5 | | B4 = B1 dilution: 1/5 | |
|---|---|---|---|---|---|---|---|
| Strain | (1) | (2) | (3) | (2) | (3) | (2) | (3) |
| Staphylococcus aureus IP 52 154 | $2 \times 10^6$ | 0 | 6.30 | 0 | 6.30 | 0 | 6.30 |

TABLE IId-continued

| Strain | Ex. 4 dilution: 1/5 | | | A4 dilution: 1/5 | | B4 = B1 dilution: 1/5 | |
|---|---|---|---|---|---|---|---|
| | (1) | (2) | (3) | (2) | (3) | (2) | (3) |
| *Pseudomonas aeruginosa* IP A22 | $1.5 \times 10^6$ | 0 | 6.17 | $2.11 \times 10$ | 4.85 | $2.1 \times 10$ | 4.85 |
| *Enterococcus faecium* IP 5 855 | $1.6 \times 10^5$ | 0 | 5.20 | $1.1 \times 10$ | 4.16 | $9 \times 10$ | 3.25 |
| *Mycobacterium smegmatis* IP 7 326 | $1.3 \times 10^5$ | 0 | 5.11 | $2.2 \times 10$ | 3.77 | $1.9 \times 10$ | 3.84 |
| *Candida albicans* IP 1180 79 | $1.8 \times 10^5$ | 0 | 5.25 | $1.9 \times 10$ | 3.98 | $1.5 \times 10$ | 4.08 |
| *Penicillium verrucosum* IP 1186 79 | $1.3 \times 10^5$ | 0 | 5.11 | $2.7 \times 10^2$ | 2.68 | $2.6 \times 10^2$ | 2.70 |
| spores of *Bacillus subtilis* var. Niger IP 7 718 (a) | $3.9 \times 10^3$ | 0 | 3.59 | $9 \times 10$ | 1.64 | $8.4 \times 10$ | 1.67 |

Notes:
(1) number of germs (or spores)/ml at time T = 0, i.e. $[S]_{\tau=0}$
(2) number of germs (or spores)/ml at time T = 2 h, i.e. $[S]_{\tau=2h}$
(3) germicidal (or sporicidal) activity, i.e. $\Delta R = \log([S]_{\tau=0}) - \log([S]_{\tau=2h})$ TABLE IIe

| Strain | Ex. 5 dilution: 1/10 | | | A5 dilution: 1/10 | | B5 dilution: 1/10 | |
|---|---|---|---|---|---|---|---|
| | (1) | (2) | (3) | (2) | (3) | (2) | (3) |
| *Staphylococcus aureus* IP 52 154 | $1.9 \times 10^6$ | $1.1 \times 10$ | 5.16 | $1.4 \times 10^2$ | 4.06 | $1.1 \times 10^2$ | 4.16 |
| *Pseudomonas aeruginosa* IP A22 | $1.5 \times 10^6$ | 10 | 5.17 | $3.7 \times 10$ | 4.61 | $1.5 \times 10$ | 4.00 |
| *Enterococcus faecium* IP 5 855 | $1.7 \times 10^5$ | 0 | 5.23 | $1.2 \times 10^2$ | 3.16 | $1.5 \times 10^2$ | 3.06 |
| *Mycobacterium smegmatis* IP 7 326 | $1.3 \times 10^5$ | 0 | 5.11 | $2 \times 10^2$ | 2.51 | $1.7 \times 10^2$ | 2.88 |
| *Candida albicans* IP 1180 79 | $1.9 \times 10^5$ | 2 | 4.97 | $3.1 \times 10^2$ | 2.00 | $3 \times 10^3$ | 2.80 |
| *Penicillium verrucosum* IP 1186 79 | $1.5 \times 10^5$ | $1.1 \times 10$ | 4.13 | $6.6 \times 10^2$ | 2.36 | $10^3$ | 2.17 |
| spores of *Bacillus subtilis* var. Niger IP 7 718 (a) | $4.1 \times 10^3$ | 0 | 3.61 | $1.4 \times 10^2$ | 1.47 | $1.8 \times 10^2$ | 1.36 |

Notes:
(1) number of germs (or spores)/ml at time T = 0, i.e. $[S]_{\tau=0}$
(2) number of germs (or spores)/ml at time T = 2 h, i.e. $[S]_{\tau=2h}$
(3) germicidal (or sporicidal) activity, i.e. $\Delta R = \log([S]_{\tau=0}) - \log([S]_{\tau=2h})$ The results in Tables IIa to IIe show that (i) in contrast to compositions A1–A5 and B1–B5, the compositions according to the invention are all fungicidal towards strains of *Penicillium verrucosum*, irrespective of the dilution, and (ii) at a given dilution, the compositions according to the invention are always more effective than compositions A1–A5 and B1–B5. These results further illustrate the synergistic effect of the combination of $H_2O_2 + RCO_2H/RCO_3H$ mixture + silver component.

Experiments II

The antiparasitic activity of the compositions according to the invention (Ex. 1–Ex. 5) was studied using parasites responsible for schistosomiasis, namely strains of *Schistosoma haematobium* (bladder schistosomiasis) and of *Schistosoma mansoni* (intestinal schistosomiasis).

At time T=0, 10 ml of the undiluted test compositions are introduced into flat-bottomed vessels of the Petri dish type, each containing 90 ml of nutrient medium and 8 to 10 parasite larvae. The number of live larvae is measured at time T=0.5 h.

The results obtained are collated in Table III below:

TABLE III

| | Number of live larvae | | | |
|---|---|---|---|---|
| | Schistosoma haematobium | | Schistosoma mansoni | |
| Product | T = 0 | T = 0.5 h | T = 0 | T = 0.5 h |
| Ex. 1 | 10 | 0 | 8 | 0 |
| A1 | 10 | 3 | 8 | 2 |
| B1 | 10 | 3 | 8 | 3 |
| Ex. 2 | 10 | 0 | 8 | 0 |
| A2 | 10 | 3 | 8 | 2 |
| B2 | 10 | 3 | 8 | 2 |
| Ex. 3 | 8 | 8 | 0 | 0 |
| A3 | 8 | 8 | 2 | 2 |
| B3 | 8 | 8 | 3 | 2 |
| Ex. 4 | 8 | 1 | 8 | 0 |
| A4 | 8 | 2 | 8 | 2 |
| B4 | 8 | 2 | 8 | 2 |
| Ex. 5 | 8 | 0 | 8 | 0 |
| A5 | 8 | 2 | 8 | 2 |
| B5 | 8 | 2 | 8 | 3 |

The results in Table III show on the one hand the value of compositions Ex. 1–Ex. 5 according to the invention compared with compositions A1–A5 and B1–B5, and on the other hand the synergistic effect of the combination of $H_2O_2$+$RCO_2H$/$RCO_3H$ mixture+silver component.

Experiments III

Experiments were carried out according to French Standard AFNOR NF T 72 180 (as amended in December 1989) in order to assess the virucidal properties of the compositions according to the invention (Ex. 1–Ex. 5) compared with the compositions of the prior art (A1–A5 and B1–B5). Briefly, the viral suspensions are brought into contact for 15, 30 and 60 minutes, at 20° C., with each test composition (i.e. "product") diluted with a phosphate buffer, and the titer of each viral suspension is then measured after the virucidal activity of said composition has been stopped by rapid dilution or, preferably, by molecular sieving. The controls received the phosphate buffer only.

Under these operating conditions, a test composition is said to be virucidal if it reduces the population of the virus in question by a factor of at least 10,000 (i.e. reduces the viral titer by a value of at least 4) compared with the control experiments.

The results obtained (mean of 5 measurements) are collated in Tables IVa, IVb and IVc below, the viral strains used being as follows:

Orthopoxvirus (vaccinia virus),
Adenovirus (human adenovirus type 5) and
Poliovirus (poliomyelitis virus 1, SABIN strain).

TABLE IVa

Viral strain: Orthopoxvirus

| Product | Viral titer, i.e. $\log([S]_{T=x})$ | | | |
|---|---|---|---|---|
| (dilution) | T = 0.25 h | T = 0.5 h | T = 1 h | Control T = 1 h |
| Ex. 1 (9/10) | ≤2.34 | ≤2.34 | ≤2.34 | 7.82 |
| A1 (9/10) | ≤2.34 | ≤2.34 | ≤2.34 | |
| B1 (9/10) | ≤2.34 | ≤2.34 | ≤2.34 | |
| Ex. 1 (½) | ≤2.34 | ≤2.34 | ≤2.34 | 7.82 |
| A1 (½) | 5.21 | ≤2.34 | ≤2.34 | |
| B1 (½) | 6.12 | 4.15 | ≤2.34 | |
| Ex. 1 (1/10) | 3.14 | ≤2.34 | ≤2.34 | 7.82 |
| A1 (1/10) | 7.60 | 6.20 | ≤2.34 | |
| B1 (1/10) | 7.80 | 6.50 | 4.50 | |
| Ex. 2 (9/10) | ≤2.34 | ≤2.34 | ≤2.34 | 7.84 |
| A2 (9/10) | ≤2.34 | ≤2.34 | ≤2.34 | |
| B2 (9/10) | ≤2.34 | 4.15 | ≤2.34 | |
| Ex. 2 (½) | ≤2.34 | ≤2.34 | ≤2.34 | 7.84 |
| A2 (½) | 5.80 | ≤2.34 | ≤2.34 | |
| B2 (½) | 7.16 | 5.44 | ≤2.34 | |
| Ex. 2 (1/10) | 3.36 | ≤2.34 | ≤2.34 | 7.84 |
| A2 (1/10) | 7.76 | 7.15 | ≤2.34 | |
| B2 (1/10) | 7.81 | 7.22 | 5.25 | |
| Ex.3 (½) | ≤2.34 | ≤2.34 | ≤2.34 | 7.83 |
| A3 (½) | 5.88 | 3.30 | ≤2.34 | |
| B3 (½) | 7.50 | 6.20 | ≤2.34 | |
| Ex. 3 (1/10) | 3.42 | ≤2.34 | ≤2.34 | 7.83 |
| A3 (1/10) | 7.80 | 7.40 | 3.27 | |
| B3 (1/10) | 7.82 | 7.30 | 5.60 | |
| Ex. 4 (½) | 3.41 | ≤2.34 | ≤2.34 | 7.82 |
| A4 (½) | 7.30 | 5.50 | 4.36 | |
| B4 (½) | 6.12 | 4.15 | ≤2.34 | |
| Ex. 4 (1/10) | 3.31 | ≤2.34 | ≤2.34 | 7.82 |
| A4 (1/10) | 7.79 | 7.20 | 5.10 | |
| B4 (1/10) | 7.80 | 6.50 | 4.50 | |
| Ex. 5 (1/10) | 3.29 | ≤2.34 | ≤2.34 | 7.83 |
| A5 (1/10) | 7.60 | 7.09 | 4.27 | |
| B5 (1/10) | 7.71 | 6.41 | 3.80 | |

TABLE IVb

Viral strain: Adenovirus

| Product | Viral titer, i.e. $\log([S]_{T=x})$ | | | |
|---|---|---|---|---|
| (dilution) | T = 0.25 h | T = 0.5 h | T = 1 h | Control T = 1 h |
| Ex. 1 (9/10) | ≤2.34 | ≤2.34 | ≤2.34 | 7.07 |
| A1 (9/10) | 4.66 | 4.35 | 4.06 | |
| B1 (9/10) | 4.41 | 4.04 | 3.71 | |
| Ex. 1 (½) | ≤2.34 | ≤2.34 | ≤2.34 | 7.07 |
| A1 (½) | 5.52 | 4.90 | 4.71 | |
| B1 (½) | 2.74 | ≤2.34 | ≤2.34 | |
| Ex. 1 (1/10) | 2.74 | ≤2.34 | ≤2.34 | 7.07 |
| A1 (1/10) | 7.17 | 5.98 | 5.36 | |
| B1 (1/10) | 6.26 | 5.49 | 5.05 | |

TABLE IVc

Viral strain: Poliovirus

| Product | Viral titer, i.e. $\log([S]_{T=x})$ | | | |
|---|---|---|---|---|
| (dilution) | T = 0.25 h | T = 0.5 h | T = 1 h | Control T = 1 h |
| Ex. 1 (9/10) | ≤2.34 | ≤2.34 | ≤2.34 | 8.44 |
| A1 (9/10) | 6.20 | 5.49 | 5.11 | |
| B1 (9/10) | 6.12 | 5.38 | 4.82 | |
| Ex. 1 (½) | ≤2.34 | ≤2.34 | ≤2.34 | 8.44 |
| A1 (½) | 6.97 | 6.31 | 5.72 | |
| B1 (½) | 6.63 | 5.47 | 5.14 | |
| Ex. 1 (1/10) | 3.64 | 2.81 | ≤2.34 | 8.44 |
| A1 (1/10) | 7.59 | 7.40 | 6.37 | |
| B1 (1/10) | 7.41 | 7.29 | 6.22 | |

The results in Tables IVa, IVb and IVc show that (i) only the compositions according to the invention are virucidal at the dilutions used (9/10, ½ and 1/10) and for the contact times used (0.25 h, 0.5 h and 1 h), and (ii) for a given dilution and a given contact time, the compositions according to the invention are generally more active than the compositions of the prior art.

Experiments IV

Complementary experiments were carried out on experimental farms (on the one hand a banana plantation contaminated by banana canker, *Colletotrichum musae*, and on the other hand an orchard contaminated by apple canker, *Nectria galligena*) with the compositions according to the invention (Ex. 1–Ex. 5) administered by spraying.

This treatment made it possible to save the diseased trees and effectively to protect the healthy trees.

Other experiments, carried out on harvests stored in silos or small wooden vats (cereals, tomatoes and dessert grapes in particular), were also able to demonstrate protection of said harvests from the customary germs which damage them.

Experiments V

Experiments were carried out with the composition of Example 6 as a hygiene product for the decontamination of balneotherapy baths, using customary hospital bacterial strains (*Pseudomonas aeruginosa, Pseudomonas cepacia, Enterobacter agglomerans, Enterobacter cloacae, Escherichia coli, Staphylococcus cohnii, Staphylococcus aureus*). It was found that, at a final use dilution of $5/10^7$, the composition of Example 6 used in this way has an effective bacteriostatic effect for at least 48 h. At the same final dilution, the comparative compositions, lacking either the component $AgNO_3$ or the mixture of $CH_3CO_2H + CH_3CO_3H$, proved ineffective.

The following experiments VI–IX are pollution control experiments carried out with dilutions of the stock composition of Example 7 and, if appropriate, the analogous compositions A7 (without $AgNO_3$) and B7 (without the mixture of $CH_3CO_2H + CH_3CO_3H$).

Experiments VI

Experiments were carried out on soils typical of the mining industry, collected in a stockyard of mining residues belonging to the Canadian company IRON ORES, soil no. 1 originating from an abandoned iron pellet works and soil no. 2 having been taken near a shut-down conveyor. The effect of diluting Ex. 7, A7 and B7 on the growth or inhibition of the heterotrophic bacteria extracted from these two soils was evaluated.

The microorganisms were extracted from each soil (5 g) with a sterile saline solution (50 ml) containing 0.85% w/v of NaCl. The resulting extract was diluted seven times in succession (1/10 dilutions). A volume of 1 ml of the extract and of each dilution was placed in a 15 ml test tube containing 8 ml of culture medium (nutrient broth at a concentration of 8 g/l) and 1 ml of a dilution (1/100, 1/10,000, 1/100,000 or 1/1,000,000) of the composition of Ex. 7, A7 or B7. The tubes were incubated at 30° C. for 3 days, the control batch receiving no test product (i.e. dilution of Ex. 7, A7 or B7).

The results obtained (means of five experiments per test composition and per test dilution) are collated in Table V below.

TABLE V

Inhibition of the heterotrophic bacteria

| Product | Total heterotrophs/g of dry soil | |
|---|---|---|
| (dilution) | in soil no. 1 | in soil no. 2 |
| Controls | $5 \times 10^5$ | $5 \times 10^6$ |
| Ex. 7 ($1/10^6$) | $5 \times 10^5$ | $3 \times 10^6$ |
| A7 ($1/10^6$) | $5 \times 10^5$ | $5 \times 10^6$ |
| B7 ($1/10^6$) | $5 \times 10^5$ | $5 \times 10^6$ |
| Ex. 7 ($1/10^5$) | $2 \times 10^5$ | $2 \times 10^6$ |
| A7 ($1/10^5$) | $5 \times 10^5$ | $5 \times 10^6$ |
| B7 ($1/10^5$) | $5 \times 10^5$ | $5 \times 10^6$ |
| Ex. 7 ($1/10^4$) | $\leq 10$ | $10^2$ |
| A7 ($1/10^4$) | 10 | $10^6$ |
| B7 ($1/10^4$) | $3 \times 10^5$ | $3 \times 10^6$ |
| Ex. 7 ($1/10^2$) | $\leq 10$ | $\leq 10$ |
| A7 ($1/10^2$) | $5 \times 10^3$ | $6 \times 10^3$ |
| B7 ($1/10^2$) | $8 \times 10^3$ | $10^4$ |

Table V shows that Ex. 7 is very effective at dilutions of $1/10^4$ and $1/10^2$ whereas A7 and B7 are unusable at the same dilutions.

Experiments VII

Experiments were carried out to study the inhibition of a pure strain of *Thiobacillus ferrooxidans* (ATCC 13661) in a liquid $(NH_4)_2SO_4$ medium containing 0.5 g/l of $MgSO_4 \cdot 7H_2O$, 0.5 g/l of $K_2HPO_4$, 33.4 g/l of $FeSO_4 \cdot 7H_2O$ and $H_2SO_4$ (to adjust the pH to 2.2).

1 ml of the suspension of the pure strain of *Thiobacillus ferrooxidans* (ATCC 13661), 8 ml of the nutrient medium and the dilution of the composition of Ex. 7 (at final dilutions of $1/10^6$, $1/10^5$, $1/10^4$ and $1/10^3$) are introduced into a test tube. The results obtained (means of 5 experiments per dilution) are collated in Table VI below, the control product not containing the dilution of Ex. 7.

TABLE VI

Inhibition of *Thiobacillus ferrooxidans*

| Product (dilution) | Number of *Thiobacillus ferrooxidans*/100 ml |
|---|---|
| Control | $7 \times 10^7$ |
| Ex. 7 ($1/10^6$) | $7 \times 10^7$ |
| Ex. 7 ($1/10^5$) | $5 \times 10^7$ |
| Ex. 7 ($1/10^4$) | $10^3$ |
| Ex. 7 ($1/10^3$) | <10 |

The results in the Table show that, at the final concentration, Ex. 7 is particularly effective for inhibiting *Thiobacillus ferrooxidans* at dilutions of $1/10^4$ and particularly $1/10^3$. In these experiments, the initial bacterial population ($7 \times 10^7$ germs/100 ml) was very considerably greater than the bacterial population normally encountered in soils in the mining industry ($10^4$ to $10^5$ germs/l).

Experiments VIII

Experiments were carried out to assess the efficacy of Ex. 7 in the oxidation of cyanides in two soils: a sterilized soil consisting of sand poor in organic matter, and a sterilized soil consisting of sand and organic matter (hereafter denoted as "organic soil"). These sterile soils were contaminated with KCN to give a final concentration of 100 mg of CN– per kg of soil.

$CuSO_4$ is incorporated as an oxidation catalyst into a dilution (1/1000, 1/100 or 1/10) of the composition of Example 7

(so as to give a final concentration of 20 mg of $Cu^{2+}$ per kg of soil). 5 ml of each dilution of Ex. 7, complemented with $Cu^{2+}$, are added to 100 g of contaminated soil, the final dilution of Ex. 7 being 0.005, 0.5 or 5 ml of Ex. 7 per kg of soil. The soils treated in this way are left to stand for 4 h at room temperature (10–25° C.), after which the cyanide concentration remaining in each soil is measured.

The results obtained have been collated in Table VII below.

TABLE VII

Cyanides remaining in the soils

| Ex. 7 | Total cyanides remaining (mg/kg) | |
|---|---|---|
| (ml/kg) | sand | organic soil |
| 0 | 27 ± 2 | 10 ± 0.5 |
| 0.005 | 21 ± 7 | 8.5 ± 1 |
| 0.5 | 3 ± 0.2 | 8.1 ± 0.5 |
| 5 | — | 4.3 ± 1.2 |

The results in Table VII show that the cyanide concentrations in the untreated soils were found to be lower than the initial concentration incorporated. This explains that other cyanide-eliminating mechanisms have taken place (atmospheric oxidation, evaporation, etc.). Said results further show that the cyanide concentration remaining in the organic soil is lower than that remaining in the sand, which is explained (i) by the fact that the pH of the sand (6.8) is different from that of the organic soil (7.4), a basic environment being more favorable to the oxidation of cyanides, and (ii) by the fact that the organic matter was able to oxidize the cyanides.

Experiments IX

Complementary experiments were carried out to assess whether or not the cleaning composition according to the invention, which inhibits the strains of *Thiobacillus ferrooxidans*, has an unfavorable effect as regards acid generation because of the presence of $H_2O_2$.

A sludge originating from a waste water treatment plant, containing a high population of *Thiobacillus ferrooxidans* and having a solids content of 20% w/v, was acidified to pH 4.0 with sulfuric acid. 75 ml samples of this sludge were placed in 250 ml flasks. Half of these flasks were sterilized to kill the bacteria present. 5 ml of various dilutions of Ex. 7 were then introduced into each flask to give final dilutions of $1/10^6$, $1/10^5$, $1/10^4$, $1/10^3$ and $1/10^2$. All the flasks were shaken (orbital shaker at 150 rpm) at 28° C. for 4 days. The pH was then measured in each flask.

The results obtained (means of 2 experiments) have been collated in Table VIII below.

TABLE VIII

Evaluation of pH of sludges

| Dilution of Ex. 7 | pH in sterile sludges (without *Thiobacillus ferrooxidans*) | pH in sludges containing *Thiobacillus ferrooxidans* |
|---|---|---|
| 0 | 3.3 | 2.6 |
| $1/10^6$ | 3.3 | 2.7 |
| $1/10^5$ | 3.3 | 2.7 |
| $1/10^4$ | 3.3 | 2.9 |
| $1/10^3$ | 3.2 | 3.0 |
| $1/10^2$ | 2.7 | 2.7 |

As regards the sludges not containing *Thiobacillus ferrooxidans* (sterilized sludges), the results in Table VIII show that (i) the pH of the sludges decreased from 4.0 to 3.3 in the absence of Ex. 7, indicating that chemical reactions, such as the natural oxidation of $Fe^{2+}$ by atmospheric oxygen, have taken place, (ii) at a final dilution less than or equal to $1/10^4$, Ex. 7 has no influence on the pH, and (iii) at a dilution of $1/10^2$, on the other hand, Ex. 7 induces acid generation.

As regards the sludges containing *Thiobacillus ferrooxidans*, the results in Table VIII show that (i) with the exception of Ex. 7 at a final dilution of $1/100$, the pH dropped to lower values than those measured in the previously sterilized samples for an identical concentration of Ex. 7, indicating a growth of *Thiobacillus ferrooxidans*, (ii) the pH drops in proportion with the concentration of Ex. 7 (i.e. the number of bacteria decreases when the concentration of Ex. 7 increases), and (iii) at a final dilution of $1/100$, Ex. 7, which should prevent the pH from dropping, induces acid generation.

In conclusion, the result of these experiments is that Ex. 7 has to be used at a final dilution of less than $1/100$ in order to avoid the effect of acid generation, a final dilution of 1/1000 being perfectly suitable.

Synergistic Effect

The interaction of the combination of $H_2O_2$+silver component+$CH_3CO_2H/CH_3CO_3H$ mixture was assessed using the method described by R. F. SCHINAZI et al., Antimicrob. Agents Chemother., 22 (no. 3), pages 499–507 (1982), and improved by J. C. POTTAGE, ibidem, 30 (no. 2), pages 215–219, (1986), and in WO-A-91/13626, taking the following definitions into account:

$IT_S$=infectious titer of the stock of strains used, $IT_A$=infectious titer of product A (in this case $H_2O_2$+ $CH_3CO_2H/CH_3CO_3H$ mixture) brought into contact with said stock, $IT_B$=infectious titer of product B (in this case $H_2O_2$+silver component) brought into contact with said stock, $T_{AB}$=infectious titer of product A+B (in this case $H_2O_2$+ $CH_3CO_2H/CH_3CO_3H$ mixture+silver component) brought into contact with said stock, $S=\log IT_S$, $A=\log IT_A$, $B=\log IT_B$, $C=\log IT_{AB}$, $Y_A=A/S=\log IT_A/\log IT_S$, $Y_B=B/S=\log IT_B/\log IT_S$, $Y_{AB}=C/S=\log IT_{AB}/\log IT_S$, and $Y_C$=product of $Y_A \times Y_B$.

There is a synergistic effect if $Y_{AB} \leq Y_C$.

On the basis of these definitions, when the values given in Table IVa are taken, for example, the comparison of the values of $Y_{AB}$ and $Y_C$ given in Table IX below is obtained.

Said Table IX shows that, at a final dilution of 1/10, the mixture of essential constituents of Ex. 1–Ex. 5 has a synergistic effect relative to A1–A5 and B114 B5, respectively, towards the viral strain of orthopoxvirus since $Y_{AB}$ is less than or equal to $Y_C$.

TABLE IX

Synergistic effect towards Orthopoxvirus at a dilution of 1/10

| Products | S | A | B | C | $Y_A$ | $Y_B$ | $Y_{AB}$ | $Y_C$ |
|---|---|---|---|---|---|---|---|---|
| Ex. 1, A1, B1 (T = 0.25 h) | 7.82 | 7.60 | 7.80 | ≦2.34 | 0.97 | 0.99 | ≦0.29 | 0.96 |
| Ex. 2, A2, B2 (T = 0.25 h) | 7.84 | 7.76 | 7.81 | 3.36 | 0.98 | 0.99 | 0.42 | 0.97 |
| Ex. 3, A3, B3 (T = 1 h) | 7.83 | 3.27 | 5.60 | ≦2.34 | 0.41 | 0.71 | ≦0.29 | 0.29 |
| Ex. 4, A4, B4 (T = 0.5 h) | 7.82 | 7.20 | 6.50 | ≦2.34 | 0.92 | 0.83 | ≦0.29 | 0.76 |
| Ex. 5, A5, B5 (T = 0.5 h) | 7.83 | 7.09 | 6.41 | ≦2.34 | 0.90 | 0.81 | ≦0.29 | 0.72 |

What is claimed is:

1. An aqueous decontaminating composition having a total weight, wherein the composition comprises:

(A) an amount of $H_2O_2$ less than or equal to 60% by weight, based on the total weight of said composition;

(B) an amount of an $RCO_3H/RCO_2H$ mixture, where R is methyl or ethyl, wherein there is a weight ratio of said mixture to the hydrogen peroxide, wherein the weight ratio of said mixture to the hydrogen peroxide is between 0.15/1 and 0.85/1;

(C) an amount of a silver component as a source of $Ag^+$ ions, wherein the silver component is selected from the group consisting of silver salts and complexes, wherein there is a weight ratio of said silver component to the hydrogen peroxide, wherein the weight ratio of said silver component to the hydrogen peroxide is between 0.0005/1 and 0.015/1;

(D) an amount of a stabilizer, wherein there is a weight ratio of said stabilizer to the hydrogen peroxide, wherein the weight ratio of said stabilizer to the hydrogen peroxide is between 0.0005/1 and 0.025/1; and an amount of water to make up to 100% by weight.

2. A composition according to claim 1 which also comprises at least one component selected from the group consisting of (E) a surfactant;

(F) a corrosion inhibitor; and (G) a fragrance.

3. A composition according to claim 1 wherein the weight ratio of the silver component to the hydrogen peroxide is between 0.0008/1 and 0.005/1.

4. A composition according to claim 1 wherein the weight ratio of the stabilizer to the hydrogen peroxide is between 0.0008/1 and 0.005/1.

5. A composition according to claim 1 which also comprises (E) an amount of a surfactant, wherein there is a weight ratio of said surfactant to the hydrogen peroxide, wherein the weight ratio of said surfactant to the hydrogen peroxide is between 0.00005/1 and 0.01/1;

(F) an amount of a corrosion inhibitor, wherein there is a weight ratio of said corrosion inhibitor to the hydrogen peroxide, wherein the weight ratio of said corrosion inhibitor to the hydrogen peroxide is between 0.00005/1 and 0.03/1; and/or (G) a fragrance in an amount less than or equal to the amount of said corrosion inhibitor.

6. A composition according to claim 1 wherein the amount of $H_2O_2$ is 1.5 to 8% by weight of the total weight of the composition;

wherein the amount of the $RCO_3H/RCO_2H$ mixture is 0.75 to 5.6% by weight of the total weight of the composition;

wherein the amount of the silver component is 0.0012 to 0.04% by weight of the total weight of the composition;

wherein the amount of the stabilizer is 0.0012 to 0.04% by weight of the total weight of the composition.

7. A composition as claimed in claim 6 further comprising:

(E) an amount of a surfactant wherein the amount of said surfactant is 0.0075 to 0.04% by weight of the total weight of the composition;

(F) an amount of a corrosion inhibitor wherein the of said corrosion inhibitor is 0.003 to 0.04% by weight of the total weight of the composition; and/or (G) a fragrance.

8. A composition as claimed in claim 1, wherein the amount of $H_2O_2$ is 7.5–8% by weight of the total weight of the composition; and wherein the $RCO_3H/RCO_2H$ mixture comprises an amount of a mixture of $CH_3CO_3H$ and $CH_3CO_2H$, wherein the amount of the mixture of $CH_3CO_3H$ and $CH_3CO_2H$ is 4.5 to 4.8% by weight of the total weight of the composition.

9. A composition as claimed in claim 1 further comprising:

(E) an amount of a surfactant wherein a weight ratio of said surfactant to the hydrogen peroxide is 0.005/1;

(F) an amount of a corrosion inhibitor wherein a weight ratio of said corrosion inhibitor to the hydrogen peroxide is between 0.001/1 and 0.005/1; and/or (G) a fragrance in an amount less than or equal to the amount of said corrosion inhibitor.

10. A method for preparing the decontaminating composition claimed in claim 1, the method comprising:

preparing a resulting mixture by mixing sufficient amounts of the water, the silver component, the stabilizer, the hydrogen peroxide, and an acid substance selected from the group consisting of $RCO_3H$, $RCO_2H$, and mixtures comprising $RCO_3H$ and $RCO_2H$, wherein the resulting mixture is the decontaminatine composition claimed in claim 1.

11. A method as claimed in claim 10, wherein the method further comprises allowing an equilibrium $$H_2O_2+RCO_2H \longleftrightarrow RCO_3H+H_2O$$

to be established in the resulting mixture.

12. A composition according to claim 1 wherein the amount of $H_2O_2$ is 7.5–8% by weight of the total weight of the composition;

wherein the RCO₃H/RCO₂H mixture comprises an amount of a mixture of CH₃CO₃H and CH₃CO₂H, wherein the amount of the mixture of CH₃CO₃H and CH₃CO₂H is 4.5 to 4.8% by weight of the total weight of the composition;

wherein the silver component comprises an amount of AgNO₃, wherein the amount of AgNO₃ is 0.008% by weight of the total weight of the composition; and wherein the stabilizer comprises an amount of H₃PO₄, wherein the amount of H₃PO₄ is 0.008% by weight of the total weight of the composition.

13. A method for preparing an aqueous decontaminating composition as claimed in claim 12, said method comprising the following steps:

(1°) providing an aqueous solution comprising the AgNO₃;

(2°) preparing a first resulting solution by introducing into the aqueous solution of AgNO₃ an aqueous solution of phosphoric acid comprising the H₃PO₄, wherein the H₃PO₄ is 85% by weight of the aqueous solution of phosphoric acid;

(3°) preparing a second resulting solution by introducing the first resulting solution at a rate of between 3 and 6 l/hr into an aqueous solution of hydrogen peroxide comprising the hydrogen peroxide, wherein the H₂O₂ is 50 to 60% by weight of the aqueous solution of the hydrogen peroxide, with stirring, at a temperature of between 0° C. and 25° C.;

(4°) preparing a third resulting solution by introducing an acid substance comprising the CH₃CO₂H at a rate of between 3 and 6 l/h into the second resulting solution, with stirring, at a temperature of between 0° C. and 25° C.;

(5°) leaving the third resulting solution to stand for 48 h in a dark area at a temperature of between 0° C. and 25° C. so that an equilibrium

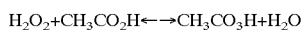

is established; and (6°) adding water to make up to 100% by weight of the composition;

wherein sufficient amounts of the H₂O₂, the CH₃CO₂H, the AgNO₃, and the H₃PO₄ are provided and/or introduced to yield the aqueous decontaminating composition claimed in claim 12.

14. A method as claimed in claim 13, wherein the temperature in step (3°) is between 4° C. and 15° C.; wherein the temperature in step (4°) is between 4° C. and 15° C.; and wherein the temperature in step (5°) is between 4° C. and 15° C.

15. A method for preparing an aqueous decontaminating composition as claimed in claim 12, said method comprising the following steps:

(1°) providing an aqueous solution comprising the AgNO₃;

(2°) preparing a first resulting solution by introducing into the aqueous solution of AgNO₃ an aqueous solution of phosphoric acid comprising the H₃PO₄;

(3°) preparing a second resulting solution by introducing the first resulting solution into an aqueous solution of hydrogen peroxide comprising the hydrogen peroxide, wherein the H₂O₂ is 50 to 60% by weight of the aqueous solution of the hydrogen peroxide;

(4°) preparing a third resulting solution by introducing an acid substance comprising the CH₃CO₂H into the second resulting solution;

(5°) allowing the third resulting solution to stand until an equilibrium

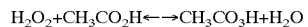

is established; and (6°) adding water to make up to 100% by weight of the composition;

wherein sufficient amounts of the H₂O₂, the CH₃CO₂H, the AgNO₃, and the H₃PO₄ are provided and/or introduced to yield the aqueous decontaminating composition claimed in claim 12.

16. A method of preparing an aqueous decontaminating composition according to claim 1, said method comprising the following steps:

(1°) providing an aqueous solution comprising the silver component;

(2°) introducing the stabilizer into said aqueous solution to yield a first resulting solution;

(3°) preparing a second resulting solution by introducing said first resulting solution into a hydrogen peroxide solution comprising the hydrogen peroxide or by introducing the hydrogen peroxide solution into said first resulting solution;

(4°) preparing a third resulting solution by introducing into said second resulting solution an acid substance selected from the group consisting of RCO₃H, RCO₂H, and mixtures comprising RCO₃H and RCO₂H;

(5°) leaving said third resulting solution until an equilibrium

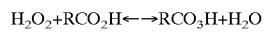

has been established; and (6°) making up to 100% by weight with water;

wherein sufficient amounts of the silver component, the stabilizer, the hydrogen peroxide, and the acid substance are provided and/or introduced to yield the aqueous decontaminating composition claimed in claim 1.

17. A method for decontaminating an industrial mining site, the method comprising adding to the industrial mining site an amount of a decontaminating composition as claimed in claim 1 in order to reduce acid generation and/or to destroy cyanides.

18. A method for decontaminating a portion of an item, the method comprising applying to the portion of the item an effective amount of the decontaminating composition claimed in claim 1.

19. A method as claimed in claim 18, wherein the item is selected from the group consisting of spaces, surfaces of materials, instruments, foodstuffs, harvests, outdoor crops, greenhouse crops, storage containers, pipelines, and drinking water.

20. A method as claimed in claim 18, wherein the portion of the item is dried after the decontaminating composition is applied.

* * * * *